(12) United States Patent
Baratz et al.

(10) Patent No.: US 10,632,001 B2
(45) Date of Patent: Apr. 28, 2020

(54) ORTHOPEDIC IMPLANT SIZING INSTRUMENTS, SYSTEMS, AND METHODS

(71) Applicant: Integra LifeSciences Corporation, Plainsboro, NJ (US)

(72) Inventors: Mark Baratz, Pittsburgh, PA (US); Jason Shultz, Liberty Township, OH (US)

(73) Assignee: INTEGRA LIFESCIENCES CORPORATION, Plainsboro, NJ (US)

( * ) Notice: Subject to any disclaimer, the term of this patent is extended or adjusted under 35 U.S.C. 154(b) by 445 days.

(21) Appl. No.: 14/970,722

(22) Filed: Dec. 16, 2015

(65) Prior Publication Data

US 2016/0175115 A1  Jun. 23, 2016

Related U.S. Application Data

(60) Provisional application No. 62/093,074, filed on Dec. 17, 2014.

(51) Int. Cl.
*A61F 2/46* (2006.01)
*A61F 2/38* (2006.01)

(52) U.S. Cl.
CPC .... *A61F 2/4657* (2013.01); *A61F 2002/3809* (2013.01); *A61F 2002/3827* (2013.01); *A61F 2002/4659* (2013.01); *A61F 2002/4661* (2013.01)

(58) Field of Classification Search
CPC ........ A61F 2/4657; A61F 2/4684; A61F 2/46; A61F 2/3804; A61F 2002/3809; A61F 2002/38; A61F 2002/3813; A61F 2002/3818; A61F 2002/3822; A61F 2002/3827; A61F 2002/3831; A61F 2002/4658; A61F 2002/4659; A61F 2002/4661; A61F 2002/4662; A61F 2002/4664

USPC .................... 33/501.45, 512; 606/102, 86 R; 623/20.11–20.13; D24/133, 155–157, D24/140

See application file for complete search history.

(56) References Cited

U.S. PATENT DOCUMENTS

| 1,157,389 | A | * | 10/1915 | Hess | ........................ G01B 3/30 |
| | | | | | 33/501.45 |
| 2,161,163 | A | * | 6/1939 | Hedgpeth | ............. B44B 5/0052 |
| | | | | | 40/629 |
| 4,211,241 | A | * | 7/1980 | Kaster | ................... A61F 2/2496 |
| | | | | | 33/512 |

(Continued)

FOREIGN PATENT DOCUMENTS

WO   WO 2014/160924 A1 * 10/2014 ........... A61F 2/3804

*Primary Examiner* — Jessica Weiss
(74) *Attorney, Agent, or Firm* — Jenkins, Wilson, Taylor & Hunt, P.A.

(57) ABSTRACT

Orthopedic implant sizing instruments, systems, and methods for use during arthroplasty procedures, for example, radial head arthroplasty procedures, are provided. The sizing instruments include at least one sizer head having at least one visualization window or slot provided therethrough for allowing a user to visualize associated surgical structures or surfaces to ensure proper joint reduction. The orthopedic implant sizing instruments, systems, and/or related methods can utilize sizer heads and/or windows having a plurality of different sizes and/or shapes.

47 Claims, 14 Drawing Sheets

(56) References Cited

U.S. PATENT DOCUMENTS

| | | | | |
|---|---|---|---|---|
| 4,240,412 | A * | 12/1980 | James | A63B 23/20 482/91 |
| 4,911,297 | A * | 3/1990 | Suburu | B25B 13/56 206/372 |
| 5,042,161 | A * | 8/1991 | Hodge | A61B 5/1076 33/501.45 |
| 5,471,756 | A * | 12/1995 | Bolanos | A61B 5/1076 33/501.45 |
| 5,489,296 | A * | 2/1996 | Love | A61F 2/2496 600/587 |
| 6,237,448 | B1 * | 5/2001 | Haxton | B25B 13/04 81/179 |
| 6,270,529 | B1 * | 8/2001 | Terrill-Grisoni | A61F 2/3804 623/18.11 |
| 6,425,920 | B1 * | 7/2002 | Hamada | A61B 17/1604 623/17.16 |
| 6,500,132 | B1 * | 12/2002 | Li | A61B 5/1076 128/898 |
| 7,172,562 | B2 * | 2/2007 | McKinley | A61B 5/103 33/511 |
| 7,608,110 | B2 * | 10/2009 | O'Driscoll | A61F 2/3804 623/20.11 |
| 7,740,661 | B2 | 6/2010 | Baratz et al. | |
| 8,945,131 | B2 * | 2/2015 | Vanasse | A61B 5/1076 606/86 R |
| 2004/0193168 | A1 * | 9/2004 | Long | A61B 17/16 606/80 |
| 2005/0075735 | A1 * | 4/2005 | Berelsman | A61F 2/3804 623/20.11 |
| 2005/0150332 | A1 * | 7/2005 | Russell | B25B 13/08 81/125.1 |
| 2010/0131022 | A1 * | 5/2010 | Vanasse | A61B 5/1076 606/86 R |

* cited by examiner

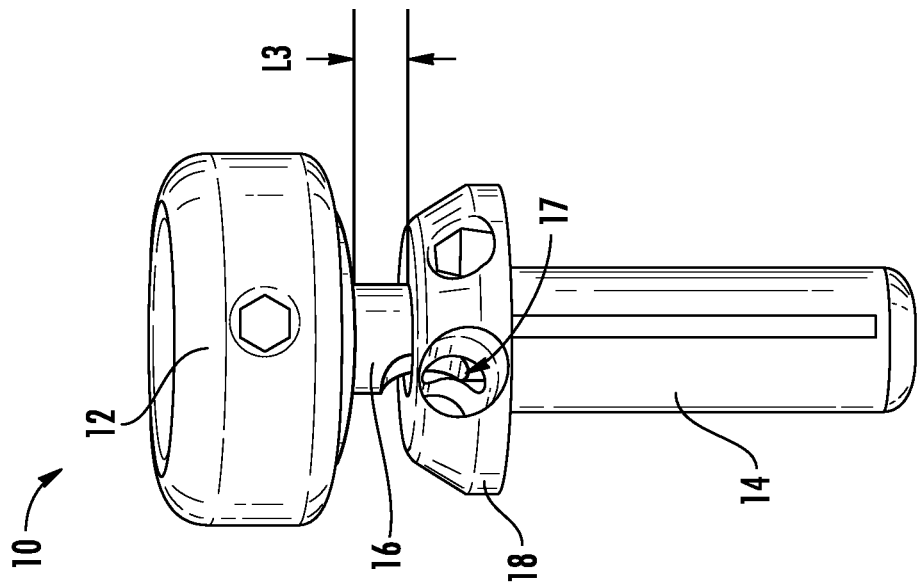
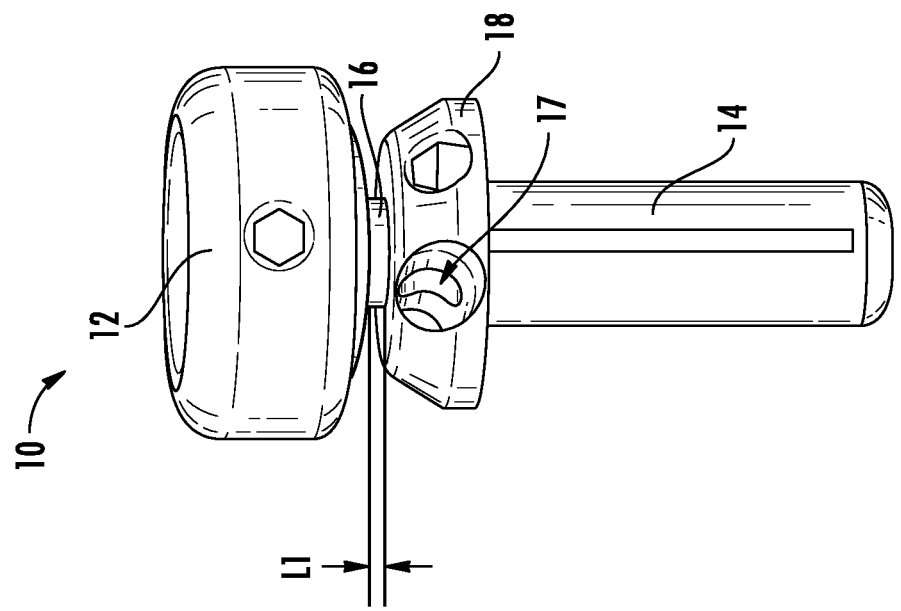

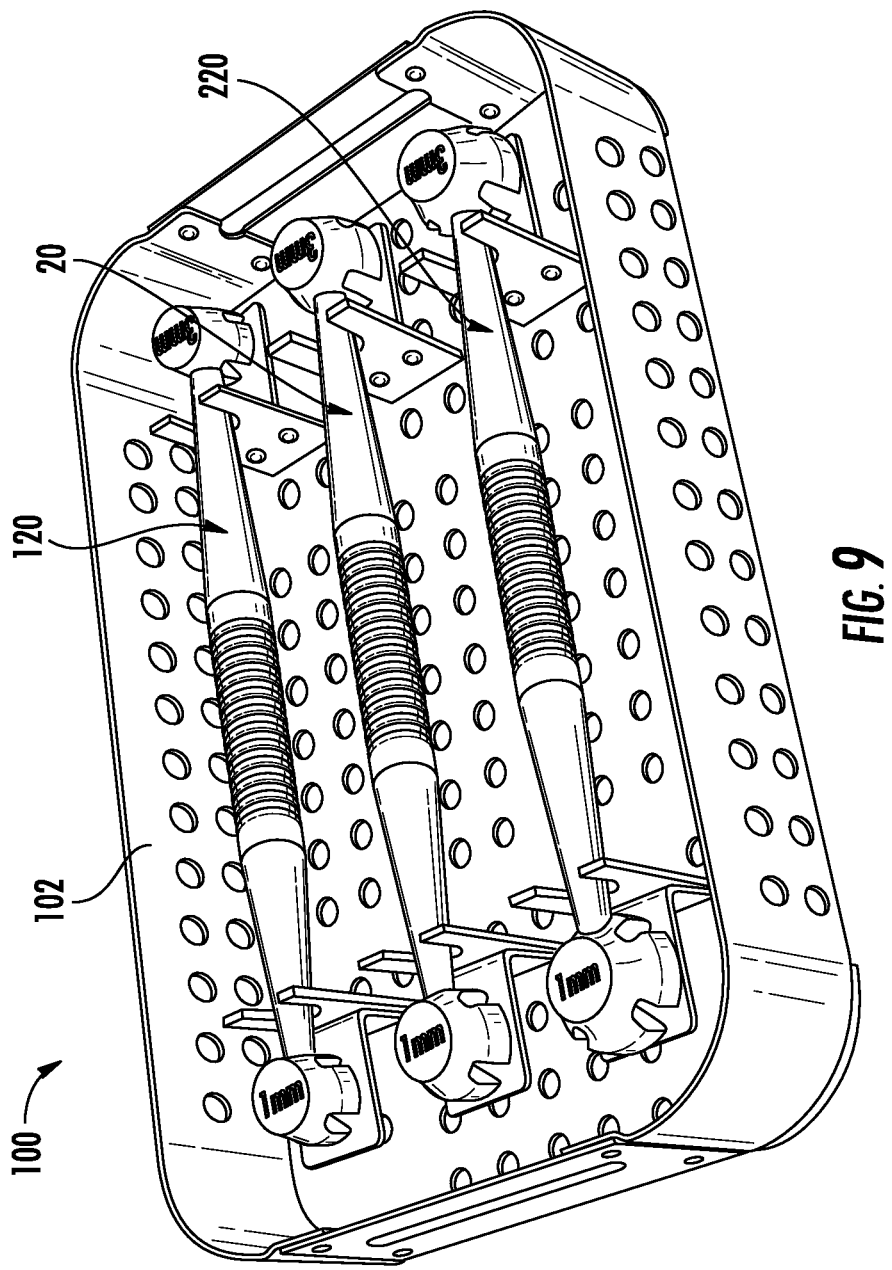

ORTHOPEDIC IMPLANT SIZING INSTRUMENTS, SYSTEMS, AND METHODS

PRIORITY CLAIM

This application claims priority to U.S. Provisional Patent Application Ser. No. 62/093,074, filed on Dec. 17, 2014, the disclosure of which is incorporated herein by reference in its entirety.

TECHNICAL FIELD

The subject matter disclosed herein generally relates to instruments for use in orthopedic surgery, and more particularly, to instruments for estimating the appropriate size of an orthopedic implant to be used during surgery, and related instrument set systems and methods.

BACKGROUND

Some fractures of the radius occur in the part of the bone that is proximate the elbow, called the radial "head". Radial head fractures are common injuries that may result from an acute elbow injury. Fractures of the radial head are typically treated with a variety of surgical and non-surgical options depending upon the severity of the injury. For example, surgical options for more severe injuries to the radial head can include open reduction with internal fixation (ORIF), radial head resection, hemi-arthroplasty (e.g., radial head arthroplasty), and total arthroplasty (i.e., total elbow replacement).

Radial head arthroplasty involves resecting the fractured and damaged radial head and replacing the natural articulation with an artificial one by use of an implant. The implant articulates with the natural cartilage surface of the capitellum of the distal humerus.

A number of radial head arthroplasty systems are commercially available. For example, the Katalyst™ Bipolar Radial Head System, available from Integra LifeSciences Corporation, headquartered in Plainsboro, N.J., includes the Katalyst™ radial head implants in various sizes as well as associated instrumentation for use in surgery. The radial head implant includes a head portion for articular engagement with a humerus bone, a stem portion for engagement with a radius bone, and a shaft for engagement with the stem portion. The head portion includes an upper surface for engaging the humerus bone. The stem portion has an axial opening for receiving at least a portion of the shaft, and a collar is disposed around the stem portion at a proximal end thereof. An upper portion of the shaft is configured to engage the head portion, while a lower portion of the shaft is elongated and cylindrically shaped for axially fitting into and moving within the axial opening of the stem portion. This commercial product, its variations, associated instrumentation, and methods for using them are described in U.S. Pat. No. 7,740,661, the disclosure of which is incorporated herein by reference in its entirety.

Prior to implantation of a radial head implant, a surgeon will need to select an implant having a size that properly fits the implant site of the particular patient. The Katalyst™ system described above contains trial stems and trial heads the surgeon can assemble and use prior to final implantation to evaluate the fit for selecting the most appropriately sized implant. The trial stems and heads in other radial head systems on the market are also solid pieces. Solid trial pieces are problematic, however, as the surgeon does not have direct visibility of resection levels below the trial piece. This may result in elbow instability problems after radial head arthroplasty.

Accordingly, a need exists for implant sizing tools with enhanced effectiveness for use in orthopedic surgery, including arthroplasty such as radial head arthroplasty.

SUMMARY

Orthopedic implant sizing instruments, systems, and related methods are provided. Orthopedic implant sizing instruments may be used to estimate the appropriate size of an orthopedic implant to be used during surgery as well as in related instrument sets (systems).

In an exemplary embodiment, an orthopedic implant sizing instrument comprises at least one visualization window or slot therein for providing visibility during arthroplasty procedures, for example, radial head arthroplasty. The sizing instrument provides a user (e.g., a surgeon) with direct visualization of the coronoid in radial head arthroplasty to ensure that resection levels are correct for proper reduction of the ulnohumeral joint. The sizing instrument may help solve or prevent elbow instability problems that sometimes occur following radial head arthroplasty.

In an exemplary embodiment, a method for sizing an implant using an orthopedic implant sizing instrument is provided. The method comprises making an incision in a patient to expose a surgical site and placing an orthopedic implant sizing instrument proximate the surgical site to determine an appropriate size of an orthopedic implant. The orthopedic implant sizing instrument can comprise a sizer head having an upper surface, a lower surface, and a peripheral wall that extends between the upper surface and the lower surface, wherein the orthopedic sizer head comprises a first window extending from a first point on the peripheral wall to a second point on the peripheral wall providing visibility therethrough. The method can further comprise placing an orthopedic implant of the appropriate size to the surgical site.

According to some embodiments of the present subject matter, the implant sizing instrument may comprise an elongated member having a first end and a second end. A first sizer head may be connected to the first end of the elongated member; the first sizer head may have an upper surface and a lower surface and may be surrounded by a peripheral wall extending between the upper surface and the lower surface. The first sizer head may have a head height from the lower surface to the upper surface. The first sizer head may comprise a first window which extends from a first point on the peripheral wall to a second point on the peripheral wall and which has a shape, width and height that allow viewing through the first window by a human eye.

In some embodiments, the window extends through the first sizer head radially or diametrically, and may have substantially parallel window walls. The sizing instrument may have two or more windows that intersect each other at an angle. In one exemplary embodiment, the sizing instrument may have two substantially perpendicular windows, which make the instrument useful for viewing surfaces of both a right and a left arm of a patient. The one or more windows may be open at the upper surface of the first sizer head, or closed, or covered either completely or partially at the upper surface of the sizer head.

In further embodiments, the sizing instrument may have multiple (e.g., two or more) sizing heads connected to the elongated member. The two or more sizer heads of the sizing instrument may be different in head circumference, head diameter, overall head height, upper surface contour, overall shape, and/or any other aspects or measurements. The two or more sizer heads may be integrally formed with the elongated member or attachable and detachable therefrom. The two or more sizer heads may comprise a metal or synthetic polymer material.

In further embodiments, the sizing instrument may include a standalone sizer head that is devoid of an elongated member or handle. Rather, a surgeon may grasp portions of the outer peripheral wall for viewing one or more exposed bones of an elbow joint, and determining an implant size. The standalone sizer head may include a sizing instrument having at least one window therethrough it that allows visibility or sight through the head for observing the bone(s) behind it.

In other aspects of the present subject matter, an orthopedic implant sizing instrument set or system is provided. The sizing instrument set may comprise a plurality of sizing instruments of the present subject matter, which may differ in sizes and/or other geometrical aspects or measurements.

In a further aspect of the present subject matter, a method for implanting an orthopedic implant in a patient in need of arthroplasty is provided. The method may comprise making an incision in the patient to expose a surgical site and using the orthopedic implant sizing instrument of the present subject matter to determine an appropriate implant size. The method may further comprise placing an orthopedic implant of the appropriate implant size into the surgical site.

In further aspects of the present subject matter, a method for sizing an implant using an orthopedic implant sizing instrument is provided. The method comprises providing a sizer head having an upper surface and a lower surface surrounded by a peripheral wall that extends between the upper surface and the lower surface. The method further comprises providing a first window that extends from a first point on the peripheral wall to a second point on the peripheral wall providing visibility therethrough. The method further comprises placing the sizer head proximate one or more surgically exposed bones of an elbow joint and looking through the first window to determine an appropriate implant size.

Other features and advantages of the present subject matter will become more apparent from the following detailed description of the subject matter, when taken in conjunction with the accompanying exemplary drawings.

BRIEF DESCRIPTION OF THE DRAWINGS

Embodiments of the presently disclosed orthopedic implant sizing instruments, systems, and methods are described herein with reference to the drawings, in which:

FIGS. 2A and 2B are perspective views of a bipolar radial head implant assembly for implantation within an elbow joint;

FIG. 9 is a system comprising an instrument tray containing a set of the three orthopedic implant sizing instruments shown in FIGS. 7A to 7C according to an exemplary embodiment of the subject matter described herein;

DETAILED DESCRIPTION

Figure 1:
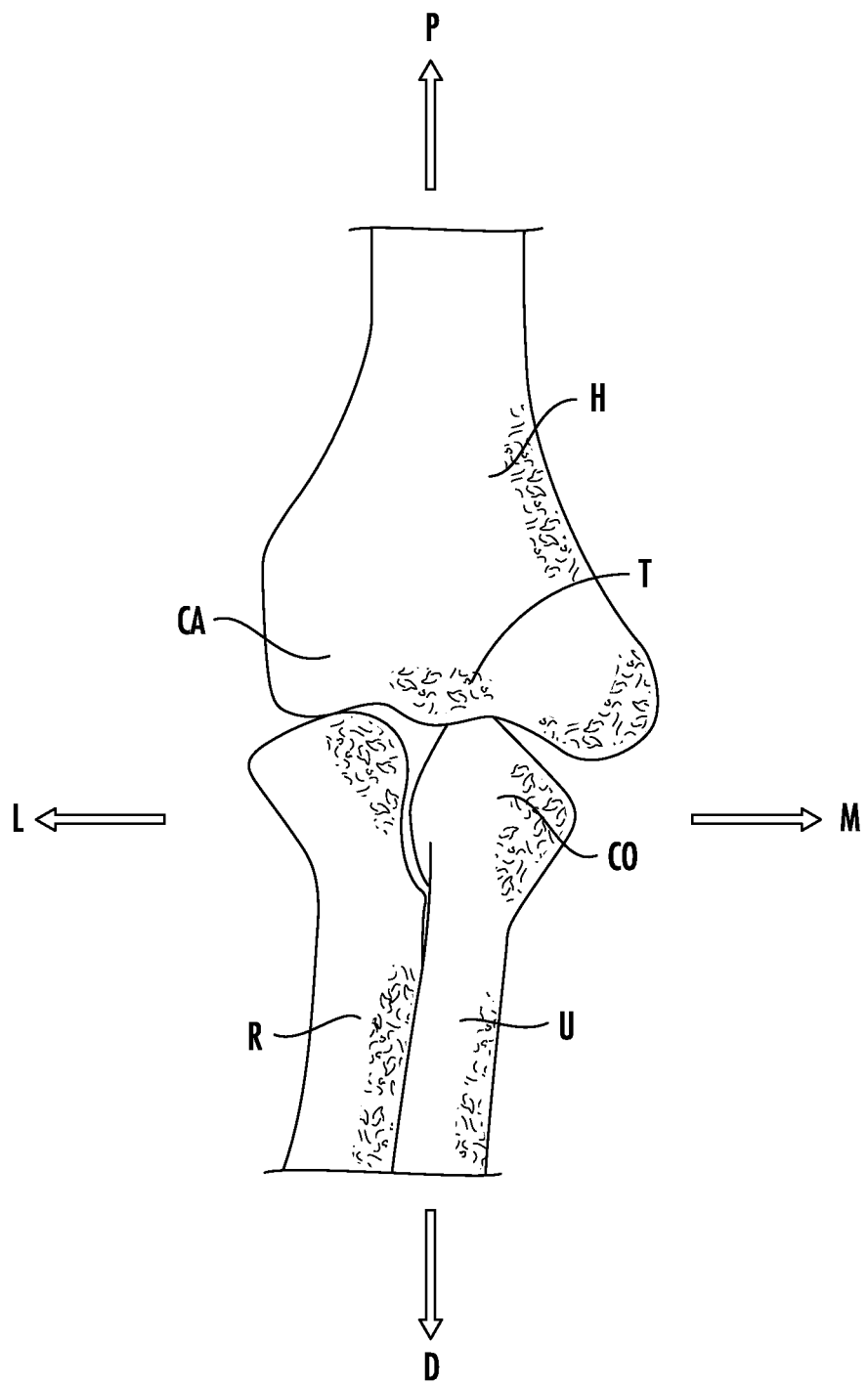
FIG. 1 is an anterior or front view of the right elbow joint.

In accordance with the present disclosure, novel orthopedic instruments, systems, and methods are provided, including orthopedic implant sizing instruments, instrument systems (sets) comprising a plurality of the sizing instruments of the present subject matter, and related methods for utilizing the instruments and systems to perform the operation of arthroplasty. Implant sizing instruments, systems, and related methods presented herein are advantageous, as sizing heads associated therewith include visualization windows or slots, which allow visibility through a portion of the sizing head for assessing underlying bone surfaces and selecting an appropriately sized implant. In certain embodiments, visualization windows are at least partially disposed in an outer wall (e.g., a lateral, exterior wall) of a sizer head for providing an unobstructed view through the sizer head for viewing underlying bone(s), bone structure(s), and/or bone surface(s).

Figures (also "FIGS.") 1 through 14 illustrate various views, aspects, and/or features associated with orthopedic implant sizing instruments, systems, and related methods. Where possible, like reference numerals designate identical or corresponding elements in each of the several views.

As used herein, the terms "sizer," "sizing instrument," and "sizing wand" are used interchangeably, and the terms "window," "slot," "visualization window," and "visualization slot" are used interchangeably.

Relative terms such as "upper", "top", "lower", or "bottom" are used herein to describe one structure's or portion's relationship to another structure or portion as illustrated in the figures. It will be understood that such terms are intended to encompass different orientations of the structures or portions in addition to the orientation depicted in the figures. For example, if the device illustrated in the figures were turned over, a structure or portion described as at an "upper" portion would now be oriented at a "lower" portion.

Unless the absence of one or more elements is specifically recited, the terms "comprising", "including", and "having" as used herein should be interpreted as open-ended terms that do not preclude the presence of one or more element.

FIG. 1 is a schematic view of the bones comprising an elbow joint, including a humerus H, a radius R and an ulna U. The term "lateral" L refers to the side with respect to outside or away from the body, while the term "medial" M refers to the other side. The term "distal" D refers to the portion of a patient's arm that is located away from the center of the body (e.g., nearer to the hand) or the portion of an instrument that is farther from the patient on which the sizer is used. The term "proximal" P refers to the portion of a patient's body that is located toward the center of the body (e.g., nearer to the shoulder) or a portion of an instrument that is closer to the patient during normal use. The terms are shown in FIG. 1 and are used to describe various aspects as relating to the elbow joint throughout.

FIG. 1 further illustrates the humeral capitellum CA, the coronoid CO of the ulna U, and the trochlea T, which may be visually assessed via orthopedic implant sizing instruments, systems, and/or methods as described herein. In certain embodiments, orthopedic implant sizing instruments, systems, and/or methods are used to view a portion of the coronoid CO and trochlea T to determine and/or verify implant size.

FIGS. 2A and 2B illustrate an implant or implant system, which may be implanted within portions of a patient's elbow joint (FIG. 1). In certain embodiments, a Katalys™ bipolar radial head system 10, which is available from Integra LifeSciences Corporation, headquartered in Plainsboro, N.J., is implanted within portions of a patient's elbow joint. Implant system 10 includes an implant head portion 12 for articular engagement with a humerus bone H (FIG. 1) and a stem portion 14 for engagement with a radius bone R (FIG. 1). Stem portion 14 includes an axial opening into which a shaft 16 can be slidably fitted. In certain embodiments, shaft 16 is configured to axially move (e.g., via telescoping) along a longitudinal axis of stem portion 14.

Implant system 10 further comprises a collar 18 disposed over and/or around stem portion 14 at a proximal end. Collar 18 has an opening 17. Opening 17 is configured to receive a screw (not shown) for preventing shaft 16 from sliding within the axial opening of stem portion 14, thereby locking head portion 12 and stem portion 14 in a relative position that provides radial head implant system 10 with a desired overall length.

In certain embodiments, telescoping the shaft 16 in and out with respect to stem portion 14 adjusts a length of radial head system 10 to a desired level of length extension, for example, with an extension length of 1 mm, 3 mm, 5 mm, 7 mm, 9 mm, etc. The length extension is a distance between a proximal surface of collar 18 and a distal surface of head portion 12. Implant system 10 shown in FIG. 2A has approximately a 1 mm length position or length extension L1, and implant system 10 shown in FIG. 2B has approximately a 3 mm length position or length extension L3. Prior to inserting implant system 10 into an elbow joint, portions of the implant system 10 and/or joint need to be sized via orthopedic implant sizing instruments, systems, and/or methods according to exemplary embodiments set forth herein.

Figure 3:
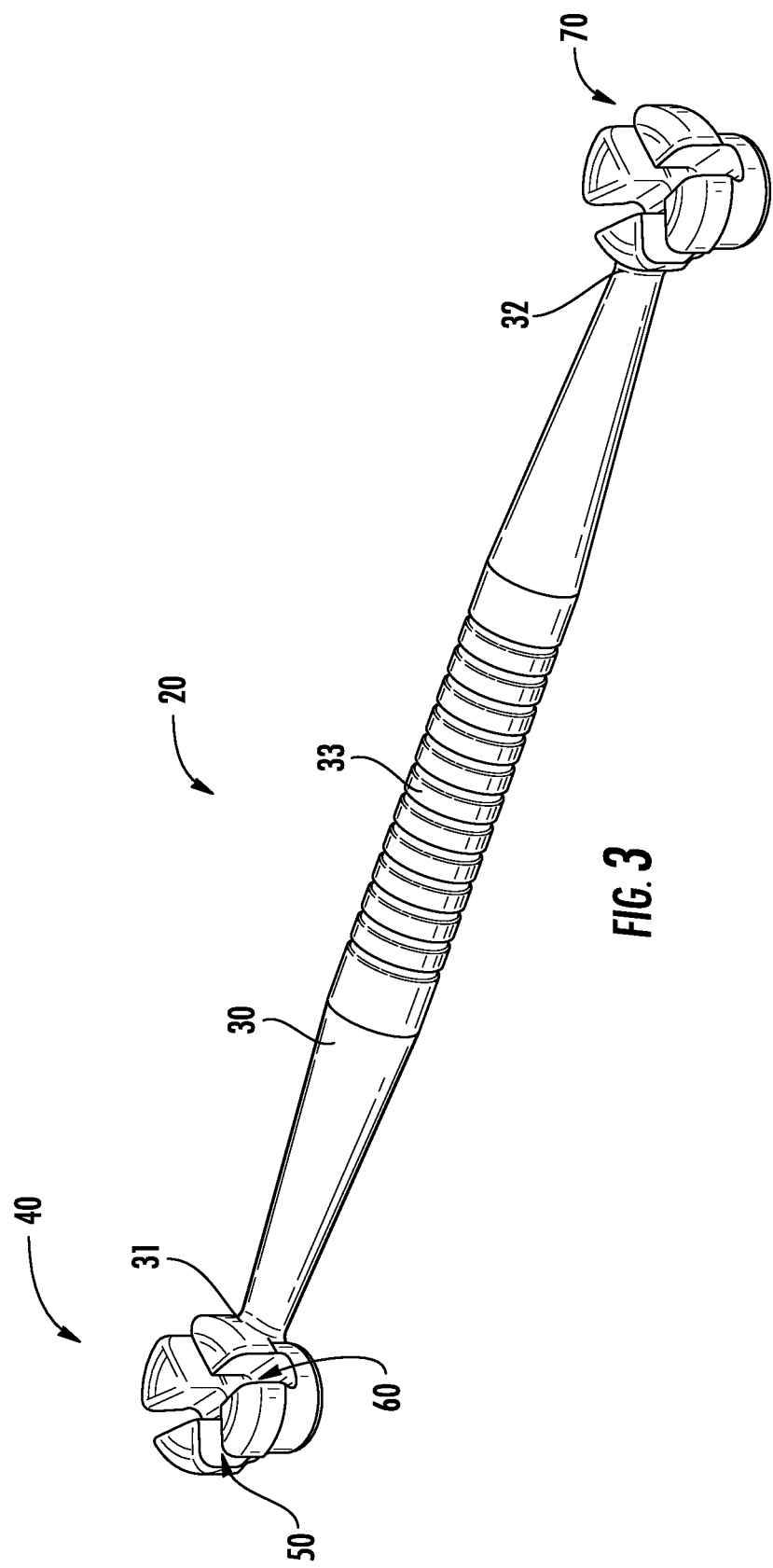
FIG. 3 is a perspective view of an orthopedic implant sizing instrument for selecting an appropriately sized implant, such as the implant shown and described in FIGS. 2A and 2B, according to an exemplary embodiment of the subject matter described herein.

Orthopedic implant sizing instruments according to a first exemplary embodiment of the present subject matter are shown in FIGS. 3, 4 and 5A-5C. Referring to FIG. 3, a first orthopedic sizing instrument generally designated 20 is shown. Sizing instrument 20 may be used to visualize bone resection surfaces for selecting an appropriate implant head height and/or implant extension length (e.g., L1, L3, FIGS. 2A and 2B).

In certain embodiments, instrument 20 comprises an elongated portion or member 30 having a first end 31 and a second end 32. Elongated member 30 may include a gripping rod, handle, or body by which a user physically grasps instrument 20 for use in evaluating bone surfaces for determining an implant size and selection prior to insertion of an implant. Instrument 20 can comprise at least a first sizer head generally designated 40 that is connected, mounted, affixed, or otherwise attached to the first end 31 of elongated member 30. In certain embodiments, instrument 20 further comprises one or more additional sizer heads, for example, a second sizer head generally designated 70 attached to second end 32. Elongated member 30 is optional; in certain aspects, sizer heads (e.g., 40 and/or 70) may be used as standalone orthopedic implant sizing instruments (see, e.g., FIG. 14). In certain embodiments, only one sizer head is provided per elongated member 30 while, in further embodiments, multiple sizer heads are provided per elongated member 30. Where provided, elongated member 30 can comprise one or more annular grooves 33 or any other surface texture or coating to facilitate improved gripping of sizing instrument 20 by a user.

Each sizer head (e.g., 40, 70) may be connected to elongated member 30 in any method or manner known to those skilled in the art. For example, first sizer head 40 and elongated member 30 can comprise a single instrument that is integrally formed. Alternatively, first sizer head 40 can comprise a discrete, separate piece that may be joined or connected to elongated member 30 directly or indirectly through another element by any mechanism in any manner conventional in the art. For example, first sizer head 40 may threadingly engage elongated member 30, frictionally engage elongated member 30, clip or lock onto elongated member 30, twist-lock against a portion of elongated member 30, or the like. Any attachment method and/or connectivity between respective first and second sizer heads 40, 70 and elongated member 30 may be provided.

Still referring to FIG. 3 and in certain embodiments, first sizer head 40 includes at least one visualization channel, groove, trench, slot, recess or window generally designated 50 by which bone surfaces may be visually observed for use in implant sizing and selection. In certain embodiments, instrument 20 can comprise multiple visualization windows, for example, at least a second window generally designated 60 by which bone surfaces may be visually observed. Providing multiple windows (e.g., 50 and 60) is advantageous because it allows one single instrument (e.g., 20) to be used for viewing surfaces of both a right arm/elbow and a left arm/elbow of a patient.

Figure 4:
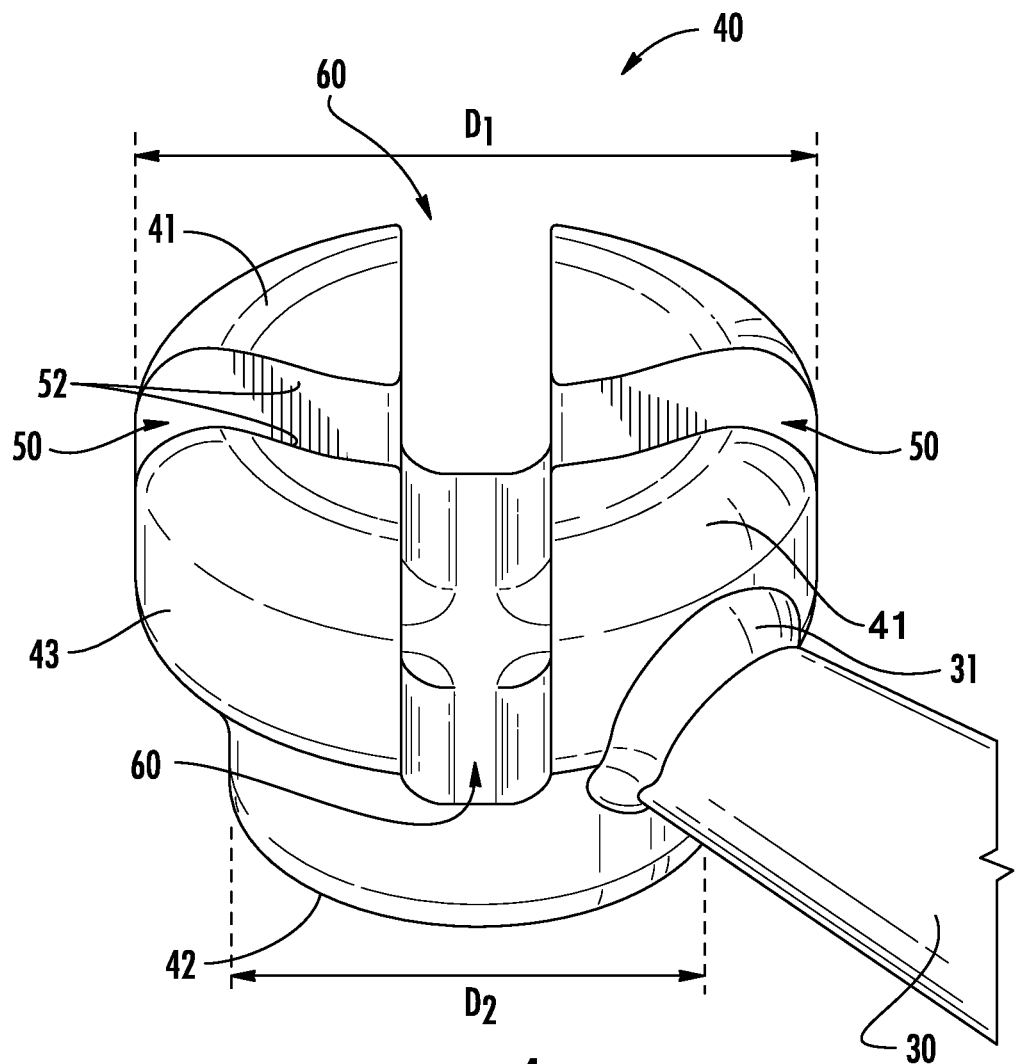
FIG. 4 is a perspective view of the first sizer head of the orthopedic implant sizing instrument shown in FIG. 3.

Referring now to FIG. 4, a more detailed view of first sizer head 40 attached to the first end 31 of elongated member 30 is illustrated. In certain embodiments, first sizer head 40 has at least one upper surface 41 and at least one lower surface 42. A peripheral wall 43 extends between upper surface 41 and lower surface 42, or portions thereof.

Peripheral wall 43 may transition in diameter as moving between upper surface 41 and lower surface 42 where desired. For example, peripheral wall 43 can comprise a first diameter $D_1$ proximate to upper surface 41 and a second diameter $D_2$ proximate to lower surface 42, where the first diameter $D_1$ may be greater than second diameter $D_2$. The variable diameter associated with first sizer head 40 is advantageous; sizer head 40 can be positioned proximate to various sized bones and/or surfaces within an elbow joint and/or spaces therebetween, as bone sizes and/or shapes may vary between patients.

Still referring to FIG. 4 and in certain other embodiments, upper surface 41 can be subdivided into multiple upper portions via at least one window 50 and one or more optional additional windows, such as second window 60. Each window (e.g., 50 and 60) may intersect upper surface 41 and include a depth relative to the thickness or height of peripheral wall 43, for example, between respective upper and lower surfaces 41 and 42. The depth of each window (e.g., 50 and 60) is a height or depth measurement in a direction substantially orthogonal to planar portions of upper and lower surfaces 41 and 42. First window 50 can have a shape, width, and height (e.g., depth) that allow viewing therethrough by a human eye. In certain embodiments, window 50 is a recessed portion of first sizer head 40, having one or more window walls 52. The one or more window walls 52 can oppose each other and be substantially parallel across a width of window 50. It is also contemplated that window walls 52 may not be parallel to each other. Window walls 52 may be substantially parallel, flare outward, taper inward, and/or be configured in any other way that allows a user to see through the window with the naked, human eye, thus providing visibility through a portion of sizer head 40. In certain embodiments, a user has visibility through a width, thickness, and/or height of sizer head 40 via windows 50 and 60, for example between upper surface 41 and lower surface 42. First and second windows 50 and 60 may include lower curved surfaces by virtue of the manufacturing processing or machining employed.

Figures 5A, 5B, 5C:
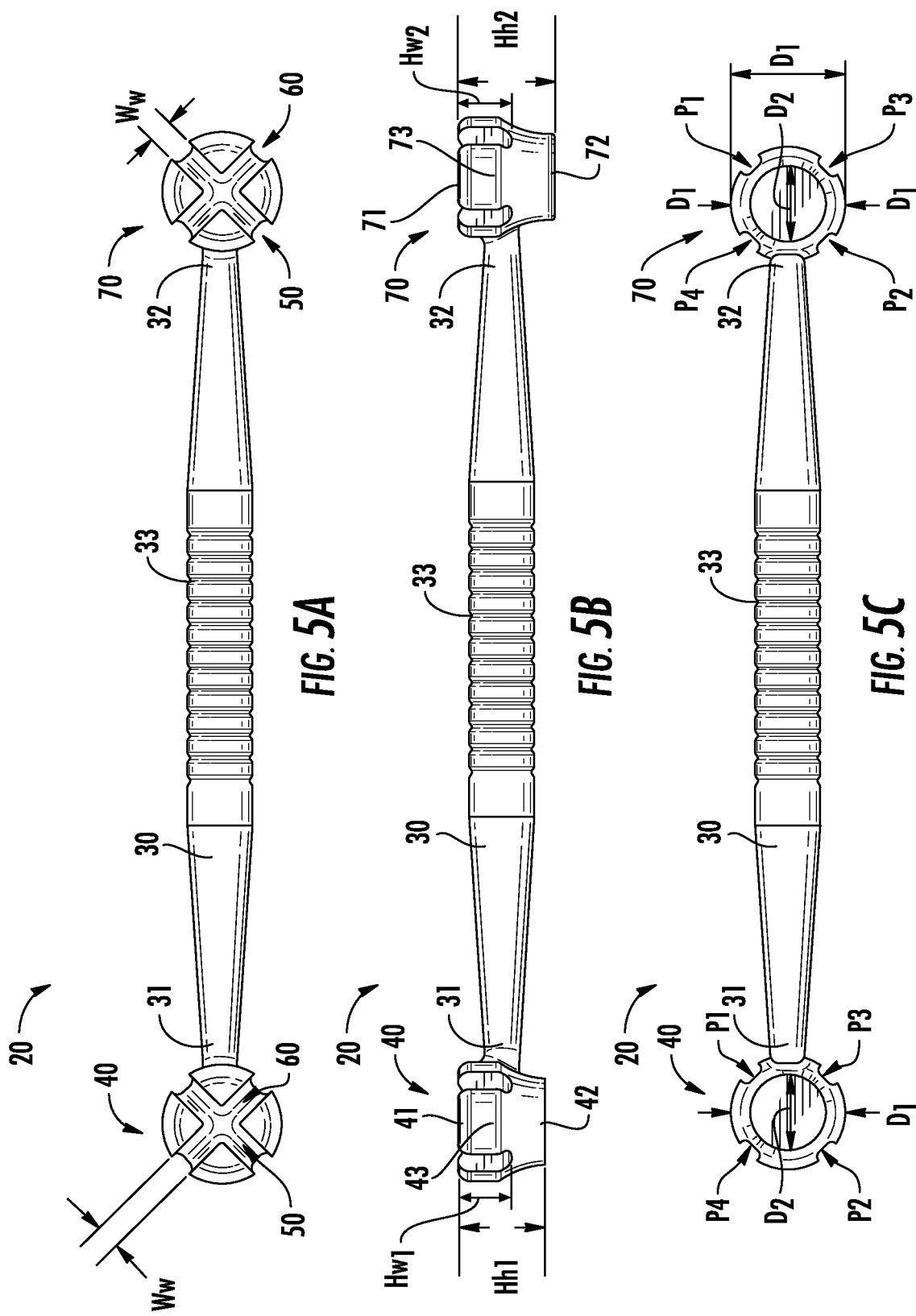
FIGS. 5A through 5C are respective top plan, front elevational, and bottom plan views of the orthopedic implant sizing instrument shown in FIG. 3.

Referring now to FIG. 5A, a top plan view of sizing instrument 20, first sizer head 40 may include at least a first window 50 and, in certain aspects, at least a second window 60, each window having a respective width $W_W$. The respective width $W_W$ of each window may be the same or different. For illustration purposes, first and second windows 50 and 60 are illustrated as having a same width, however multiple different windows having multiple different widths are contemplated. Similarly, first and second sizer heads 40 and 70 may each have at least a first window (e.g., 50), where the first windows are either a same width or a different width. Second sizer head 70 may also include two or more windows arranged substantially the same configuration as first sizer head 40 described in FIG. 4.

In certain embodiments, first window 50 and second window 60 of first sizer head 40 can each include a width $W_W$ as measured across upper surface 41 of sizer head 40. The window width $W_W$ may depend upon the diameter of the sizer head. In certain embodiments, $W_W$ is approximately 3.7 millimeters (mm) on an 18 mm sizer head (140, FIGS. 7A, 8A), approximately 4.3 mm on a 21 mm sizer head (e.g., 20, FIG. 3), and/or approximately 4.3 mm on a 24 mm sizer head (e.g., 240, FIGS. 7C, 8C). Windows 50, 60 of any size, shape, and/or orientation or configuration are contemplated.

In FIG. 5B, a front elevational view of sizing instrument 20, first sizer head 40 can comprise a respective head depth or head height Hh1 as measured between lower surface 42 and upper surface 41, or respective portions thereof. Second sizer head 70 can comprise a respective head depth or head height Hh2 as measured between lower surface 72 and upper surface 71, or respective portions thereof. In certain embodiments, head height Hh1 of first sizer head 40 may be different from head height Hh2 of second sizer head 70. For example, head height Hh1 of first sizer head 40 may be dimensionally larger or smaller than head height Hh2 of second sizer head 70.

Still referring to FIG. 5B and in other embodiments, first and second windows 50 and 60 may be oriented orthogonally to each other. First and second windows 50 and 60 may each bisect upper surfaces 41 and/or 71 of respective sizer heads 40 and/or 70. Each window (e.g., 50, 60) can form a recessed groove or a recessed channel in upper surface 41 and/or 71 of respective sizer head 40 and/or 70. First and/or second windows 50 and 60 can comprise a depth or a height relative to the overall height of sizer head 40 and/or 70 (e.g., respective to Hh1, Hh2). Windows 50, 60 of first sizer head 40 may be substantially equal to or different from windows at second sizer head 70. For example, windows 50, 60 of first sizer head 40 may differ in size (e.g., width, depth, height, or the like) and/or shape compared to windows 50, 60 at second sizer head 70 in embodiments where a second sizer head is provided.

In certain embodiments, each window 50, 60 at first sizer head 40 comprises a depth or height of Hw1. Each window 50, 60 at second sizer head 70 comprises a depth or height of Hw2. Respective window heights (Hw1, Hw2, etc.) may measure approximately 10% or more of the overall height (e.g., Hh1, Hh2) of the respective sizer head, approximately 25% or more of the overall height of the respective sizer head, approximately 50% or more of the overall height of the respective sizer head, or more than 75% of the overall height of the respective sizer head.

FIG. 5C is a rear or bottom plan view of sizing instrument 20 which opposes the front or top plan view as shown in FIG. 5A. Respective first and second sizer heads 40 and 70 can comprise a first window 50 or slot, which extends from a first point P1 on the respective sizer head circumference or peripheral walls 43 and 73 to a second point P2 on the respective sizer head circumference or peripheral walls 43 and 73. First point P1 and second point P2 may oppose each other across respective peripheral walls 43 or 73 and, in some aspects, first point P1 may be directly across from (i.e., one-half of a rotation, or 180°) second point P2. For example, first point P1 may directly oppose second point P2. In the embodiment shown in FIG. 5C, first and second sizer heads 40 and 70 have circular upper and lower surfaces in a planar view, each surface having respective first and second diameters $D_1$ and $D_2$. First point P1 and second point P2 diametrically oppose each other across each of the respective first and second diameters $D_1$ and $D_2$. Instrument 20 includes a size-specific sizing wand which includes at least one sizer head and, in certain embodiments, multiple sizer heads connected by an intermediate handle (e.g., 30). Each sizer head may be a same size or a different size. Each sizer head may include one or more windows that are a same size (e.g., width, depth, height, etc.) or different sizes and/or shapes.

Still referring to FIG. 5C, the respective first and second sizer heads 40 and 70 of sizing instrument 20 may have a second window 60 which extends from a third point P3 on the respective peripheral walls 43 or 73 to a fourth point P4 on the respective peripheral walls 43 or 73. Like first window 50, second window 60 may be configured to allow viewing therethrough by a human eye. In addition, like first window 50, third point P3 and fourth point P4 may be on opposite sides of the respective peripheral wall 43 or 73. For example, third point P3 and fourth point P4 may directly oppose each other across a diameter of the respective sizer head. In the embodiment as shown, third point P3 and fourth point P4 diametrically oppose each other across the respective sizer head.

As shown in FIGS. 5A through 5B, second window 60 may intersect first window 50 at an angle. In the exemplary embodiments shown, first window 50 and second window 60 are perpendicular to each other. It is contemplated that the two windows 50, 60 may intersect at any angle of more than approximately 0° and less than approximately 180°, for example, the two windows may intersect at between approximately 30° to approximately 150°, at between approximately 45° to approximately 135°, at between approximately 60° and approximately 120°, and at approximately 90°. The two intersecting windows may be orthogonally oriented for providing a sizing instrument 20 useful for viewing different directions and/or different sides of the body. For example, exemplary instrument 20 is useful for both a right and left arm of a patient by virtue of multiple sizer heads having multiple sizing windows.

FIGS. 5A through 5C generally illustrate elongated member 30 constituting a handle to be held by the user. The handle may have annular grooves 33 or any other surface texture or coating to facilitate gripping of the sizing instrument 20 by the user. The handle may be of any size (e.g., length, diameter, etc.), shape (e.g., rod, shaft, spoke, etc.) and/or configuration suitable for being held by a user. The grooves 33 illustrated in FIGS. 5A through 5C may be substituted with other surface texture(s), including, but not limited to, a knurled surface, a textured surface, a non-slip coated surface, etc. It is also possible that instrument 20 has more than two sizer heads (e.g., three or more sizer heads, four or more sizer heads, etc.). It is also possible that instrument 20 is configured to receive multiple different sizes of sizer heads (e.g., different sizes of sizer heads may attach and detach from elongated member 30). It is also possible that the first sizer head 40 has more than two windows, so long as the size of the sizer head and manufacturing process allow.

Notably, each window (e.g., 50, 60) as described herein has a shape, width and a height (depth) relative to the sizer head that allow viewing therethrough by the human eye. The walls (e.g., 52, FIG. 4) of each window may be parallel or non-parallel. Windows may include a groove, a channel, a slot, a trench, an aperture, or an opening. As persons of skill in the art will appreciate, windows (50, 60) may have any size, shape, and/or configuration other than that shown, which are configured to provide visibility through the window and/or portions of the respective sizer head with a naked human eye. The one or more windows or slots (e.g., 50, 60) of each respective sizer head (e.g., 40, 70) may intersect the upper surface (e.g., 41, 71) of the sizer head such that each window or slot is open at the upper surface. In alternative embodiments, the windows may be closed or covered completely or partially at the upper surface of the sizer head. Any configuration may be provided and the listing above is not exhaustive.

Referring to FIGS. 5A through 5C in general, sizing instrument 20 may have one or more sizing/sizer heads connected to elongated member 30. The two or more sizer heads of sizing instrument 20 may differ in at least one aspect, for example, in head height (e.g., Hh1 differs from Hh2), head circumference, head diameter, window size, window shape, window configuration, upper or lower surface curvature or contour, overall shape, any other geometrical aspect or measure, or one or more combinations thereof. Varying sizer heads maximizes the potential of using a single sizing instrument 20 for reducing the total number of sizing instruments required to select an appropriately sized implant from a range of differently sized implants. The sizer heads of sizing instrument 20 may be configured to adequately represent or conform to the geometry of the implants (e.g., 10, FIGS. 2A and 2B).

In certain embodiments, an optional second sizer head 70 is connected to second end 32 of elongated member 30. Like first sizer head 40, second sizer head 70 has an upper surface 71 and a lower surface 72 that are surrounded by a peripheral wall 73 extending therebetween. Second sizer head 70 has a head height Hh2 from the lower surface 72 to the upper surface 71. Like the sizer head 40, second sizer head 70 comprises one or more windows. The general configurations and variations of the one or more windows in the first sizer head 40 apply to the one or more windows in the second sizer head 70.

In an exemplary embodiment, first sizer head 40 and second sizer head 70 differ in head height (e.g., Hh1, Hh2) to represent the different length positions of the radial head system. In certain embodiments, first sizer head 40 has a head height Hh1 that represents a 1 mm length position of the Katalyst™ radial head system (e.g., L1, FIG. 2A), and sizer head 70 has a head height Hh2 that represents a 3 mm length position (e.g., L3, FIG. 2B) of the Katalyst™ radial head system. The sizing instruments for use with the Katalyst™ radial head system (FIGS. 2A, 2B) described above are exemplary embodiments, for illustration purposes only. The sizing instruments of the present subject matter may be used with and/or for sizing other orthopedic implant systems by configuring the sizer heads to represent the geometry of the particular orthopedic implants.

It will be appreciated that FIGS. 3 through 5C are presented for illustrative purposes and that additional sizes of sizer heads and/or instruments other than those depicted in FIGS. 3 through 5C can be used for determining and verifying implant sizing. Additionally, it will be appreciated that various structures depicted in FIGS. 3 through 5C can be separated or combined.

Figure 6A:
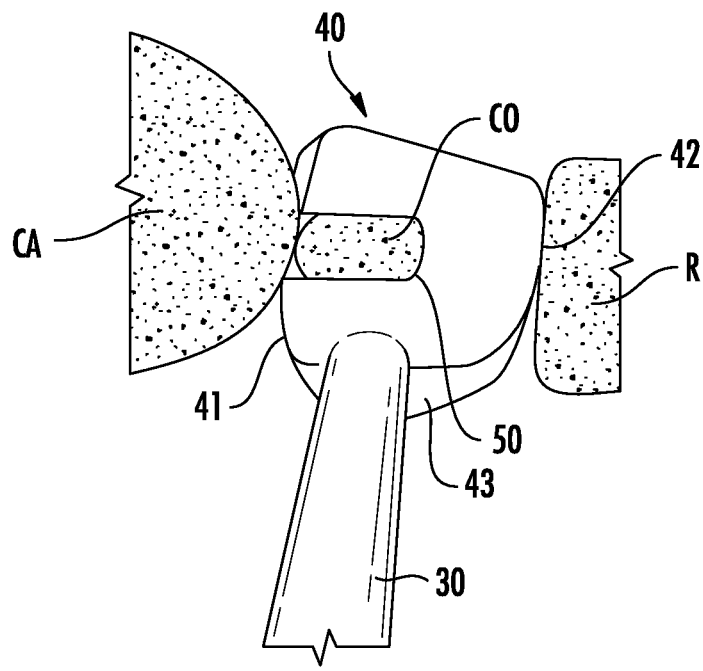
FIG. 6A is a schematic illustration of coronoid visualization via the orthopedic implant sizing instrument shown in FIG. 3 when the bone resection level and the head height selection are correct according to an exemplary embodiment of the subject matter described herein.
Figure 6B:
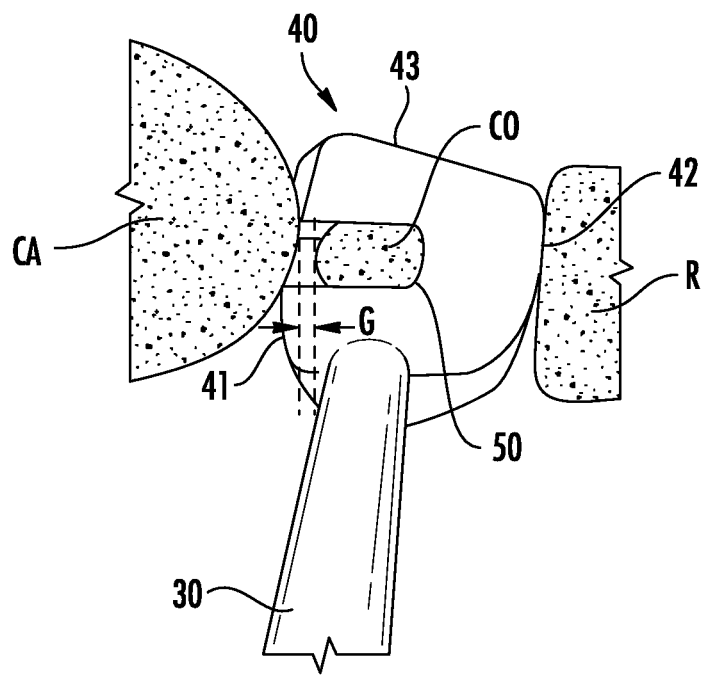
FIG. 6B is a schematic illustration of a gap visualization via the orthopedic implant sizing instrument shown in FIG. 3 when the length of the proposed implant is incorrect according to an exemplary embodiment of the subject matter described herein.

FIGS. 6A and 6B schematically illustrate providing sizing instrument 20 for use during radial head replacement surgery following resection of a radial shaft but prior to implantation of the final implant (e.g., 10, FIGS. 2A, 2B). In certain embodiments, sizing instrument 20 is inserted into a joint space with the proximal articular surface or a portion thereof (e.g., 41) contacting the humeral capitellum Calif. and the distal flat face (e.g., 42) contacting the resected radius bone R. Window 50 in the sizer head 40 allows visualization through the sizer head, for example, and allows visualization of the coronoid CO of the ulna U (FIG. 1), which is medial to the radial head. Visualization of the coronoid CO of the ulna U helps ensure that the radial shaft resection level is correct when the coronoid CO sits flush with the trochlea T (FIG. 1) such that the ulnohumeral joint is properly reduced. The bone resection and implant head length position (e.g., L1, L3, etc.) or height selection should be correlated to ensure optimal post-operative joint function. The bone resection and head height selection are correct if the coronoid CO is contacting the trochlea T.

FIG. 6A depicts how the coronoid CO should look as viewed through window 50 of sizer head 40 of the sizing instrument 20 when the bone resection level and head height selection are correctly matched. FIG. 6B depicts a scenario where the proximal edge of the coronoid CO is pushed distal to the proximal edge of the sizer head 40, creating a gap G between the coronoid CO and trochlea (T in FIG. 1). This suggests that the length of the proposed implant selected is too long, which may result in overstuffing the joint and instability after surgery.

FIGS. 7A through 7C and 8A through 8C illustrate various sizes and/or geometric configurations associated with sizing instruments disclosed herein. Each sizer head (e.g., 40, 70, FIGS. 5A through 5C) may differ in size, shape, and/or respective window aspects because each sizer head may include geometry that is representative of a final implant. Sizer heads may differ in regards to the head diameter, articular surface radius, total head height, window width, window depth or height, window shape, or the like. As noted above, the Katalyst™ radial head system (e.g., 10, FIGS. 2A, 2B) has a telescoping stem, which allows intraoperative adjustment to one of five predetermined height settings, e.g., 1 mm, 3 mm, 5 mm, 7 mm, and 9 mm.

Figure 7A:
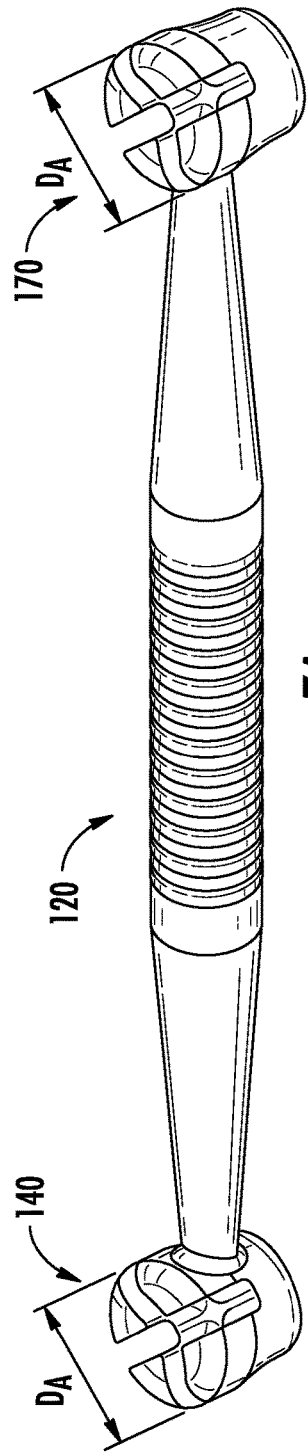
FIGS. 7A through 7C are respective perspective views of orthopedic implant sizing instruments having different sizer heads according to exemplary embodiments of the subject matter described herein.

The sizing instrument generally designated 120 in FIG. 7A has a head diameter $D_A$ of approximately 18 mm for a Katalyst™ radial head implant that has the same head diameter. Sizing instrument 120 has two sizer heads 140, 170 for the 1 mm and 3 mm height selections, respectively. Each sizer head 140, 170 may include approximately a same diameter $D_A$.

Figure 7B:
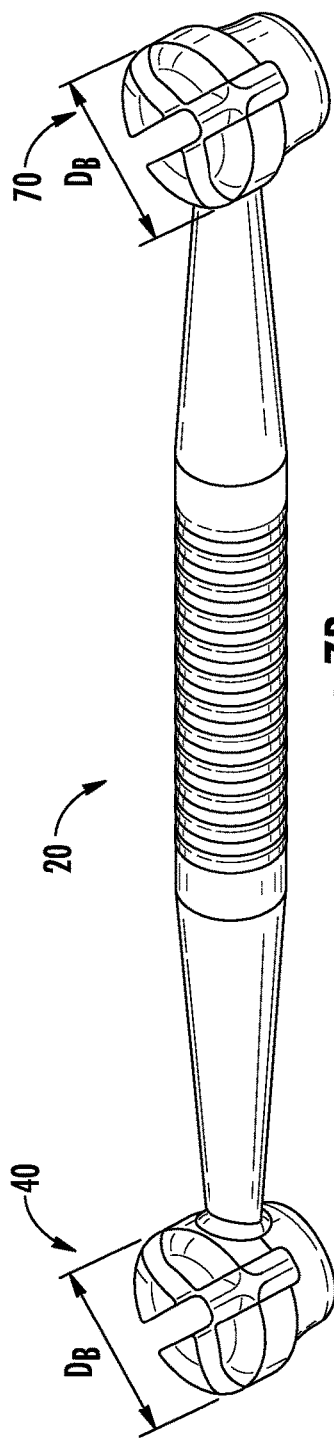

Sizing instrument 20 (e.g., FIG. 3) has a head diameter of approximately 21 mm and is shown again in FIG. 7B in a perspective view. The sizing instrument 20 is for a Katalyst™ radial head implant that has a 21 mm head diameter $D_B$. Sizing instrument 20 has two sizer heads 40, 70 for the 1 mm and 3 mm height selections, respectively. Each sizer head 40, 70 may include approximately a same diameter $D_B$.

Figure 7C:
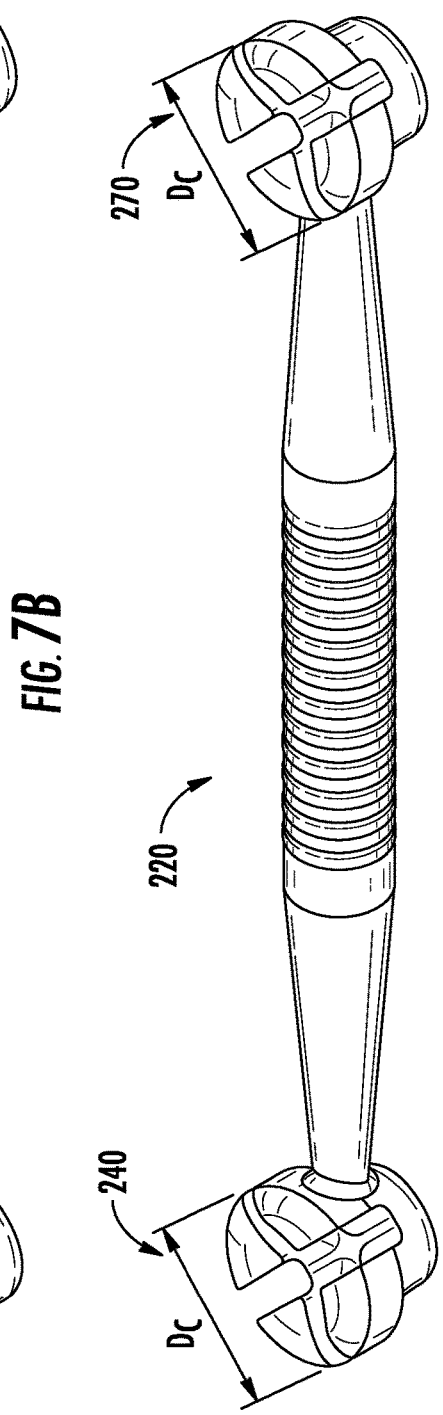

The sizing instrument 220 shown in FIG. 7C has a head diameter of approximately 24 mm for a Katalyst™ radial head implant that has the same head diameter $D_C$. Sizing instrument 220 has two sizer heads 240, 270 for the 1 mm and 3 mm height selections, respectively. Each sizer head 240, 270 may include approximately a same diameter $D_C$. For FIGS., 7A to 7C, additional sizing instruments and/or sizer heads may be provided for representing any other additional implant head height(s) or other geometrical selection(s).

Figure 8A:
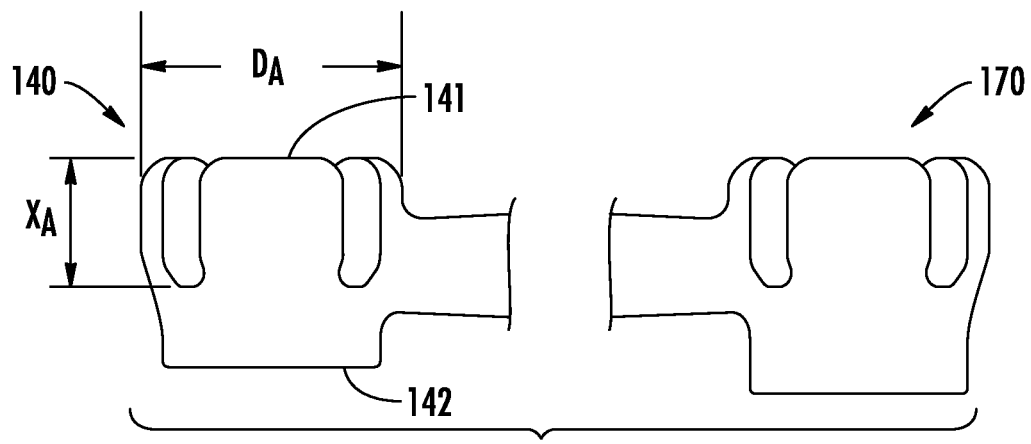
FIG. 8A depicts the first and second sizer heads of the orthopedic implant sizing instrument shown in FIG. 7A respectively.
Figure 8B:
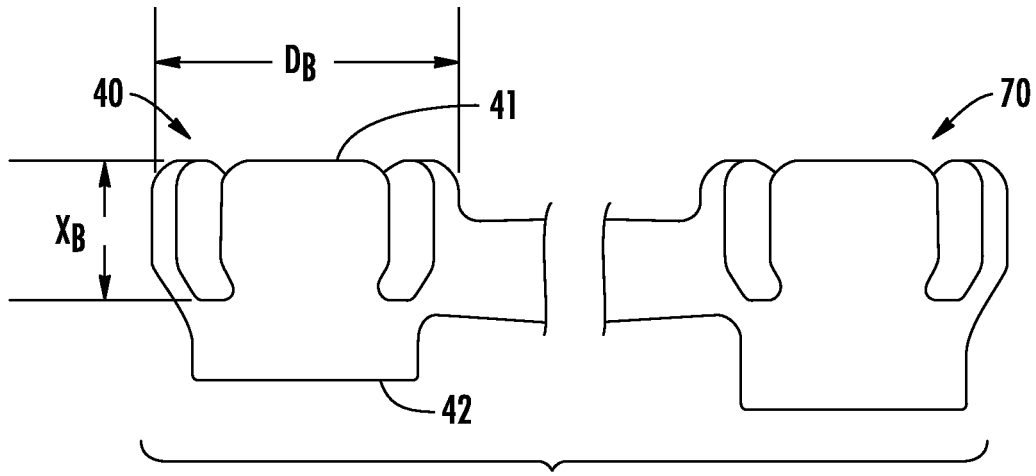
FIG. 8B depicts the first and second sizer heads of the orthopedic implant sizing instrument shown in FIG. 7B respectively.
Figure 8C:
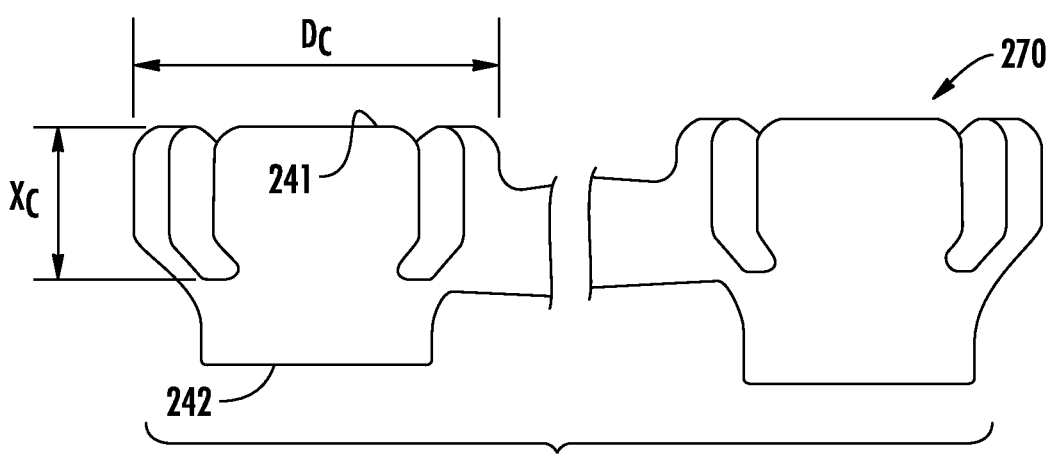
FIG. 8C depicts the first and second sizer heads of the orthopedic implant sizing instrument shown in FIG. 7C respectively.

FIGS. 8A to 8C illustrate closer views of sizer heads in FIGS. 7A to 7C, respectively. As FIGS. 8A to 8C illustrate, respective windows extend down from the top surface a given distance (e.g., depth or height) with respect to the overall head height of the respective sizer head. The window may extend approximately half (e.g., 50%) of the overall head height, or less than or more than half of the head height, for example, in a range between about 50% to about 65% of the head height depending on size of the sizer head. Window heights or depths (e.g., $X_A$ to $X_C$) do not necessarily need to be constant along a length thereof, thus walls of the windows may flare, taper, curve, round, or be non-linear, so long as the height variances do not inhibit visualization through the respective window.

FIG. 8A illustrates a window comprising a window height or depth $X_A$ with respect to the overall head height. Depth $X_A$ may be about 9 mm or more for an 18 mm sizer head, such as sizer head 140. Depth $X_A$ may extend between an upper surface 141 of sizer head 140, and a lower surface 142 thereof. Any depth $X_A$ may be provided.

FIG. 8B illustrates a window comprising a window height or depth $X_B$ with respect to the overall head height. Depth $X_B$ may be about 9.5 mm or more for a 21 mm sizer head, such as sizer head 40, and extend between upper surface 41 and lower surface 42.

FIG. 8C illustrates a window comprising a window height or depth $X_C$ with respect to the overall head height. Depth $X_C$ may be about 10 mm or more for a 24 mm sizer head, such as sizer head 240. Depth $X_C$ may extend between an upper surface 241 of sizer head 240, and a lower surface 242 thereof. Any depth $X_C$ may be provided.

In another aspect of the present subject matter, a system 100 of sizing instruments is provided. System 100 may include a set of sizing instruments disposed therein, where one set may include a plurality of different sizes of sizing instruments. FIG. 9 is one exemplary embodiment of an orthopedic sizing instrument system 100 comprising a plurality of sizing instruments 20, 120, 220. The various sizing instruments 20, 120, 220 may optionally be color-coded for convenient size differentiation by a prospective user. The instruments may be contained in a sizing instrument container 102 or in a larger instrument tray (not shown), that also contains other surgical instruments for arthroplasty.

In certain embodiments, the three sizing instruments in system 100 may include head diameters (e.g., $D_A$, $D_B$, $D_C$, FIGS. 7A to 7B) of approximately 18 mm, approximately 21 mm, and approximately 24 mm, respectively. The two sizer heads on each sizing instrument may have a same head diameter, however, the overall head heights and/or window depths may differ. One end of each instrument 20, 120, 220 (FIGS. 7A through 7C) may optionally be labeled with the size (e.g., 1 mm) of one implant extension length and the other end of each respective sizing instrument may optionally be labeled with the size (e.g., 3 mm) of another implant extension length. Where labeled, the label may be engraved on the bottom flat side of the respective sizer heads. These values represent the amount of spacing between the stem portion (e.g., 14, FIGS. 2A, 2B) and the head portion (e.g., 12, FIGS. 2A, 2B) of the radial head system or implant system (e.g., 10, FIGS. 2A, 2B) when the parts are assembled intraoperatively. Thus, a user selects an implant size (e.g., FIGS. 2A, 2B) and extension length using sizing instruments described herein.

Radial head arthroplasty can include assessing elbow stability using commonly accepted practices such as preoperative radiographs, intraoperative inspection, and stress radiographs. During surgery, the surgical wound site may be exposed by making an incision through the skin, muscle, tendon and ligament as necessary, and resecting the radial head. An appropriately sized diameter trial head may be chosen based on reassembly of the fracture components using a head sizing fixture as a template. The intramedullary canal of the proximal radius may be opened, and the proximal radius may be broached to create a smooth cut end of the proximal radius with a reamed intramedullary canal that is parallel to the long axis of the radius.

Another step includes using the sizing instrument of the instant subject matter to establish a proper fit. Once the appropriate diameter radial head trial has been selected, the corresponding color-coded sizing wand should be used to confirm the radial neck resection length. Remove the sizing wand from the instrument container 102 and system 100 shown in FIG. 9. There may be at least two sizes per wand (e.g., 20, 120, 220), corresponding to the 1 mm and 3 mm radial neck resection lengths. The values of 1 mm and 3 mm do not correlate to the actual head height of the implant, but rather the distance between the distal face of the head portion and the proximal face of the collar (e.g., L1, L3, FIGS. 2A and 2B).

When measuring the length, the user should ensure that the ulnohumeral joint is concentrically reduced. This can be determined by confirming that the lateral aspect of the coronoid CO (FIG. 6A) is sitting flush with the lateral trochlea as visualized through the window of the sizing wand. With the elbow positioned in 90° of flexion and neutral forearm rotation, the chosen sizer head (18 mm, 21 mm or 24 mm in head diameter; 1 mm or 3 mm extension length) should slide into the space between the cut end of the radial neck and the capitellum without significant force. This reflects the appropriate radial neck resection for the length of the replacement. The sizing wand is advanced until it is seated on the radial notch of the ulna. The distal aspect of the sizing wand should contact the cut end of the radial neck. If the sizing wand does not fit, then more bone resection will be needed for this size implant. If the sizing wand is too short for the cut length, a sizing wand corresponding to a larger radial neck resection length can be tested. This will aid in determining whether a 1 mm or 3 mm telescoping distance is appropriate during final implant positioning. When inserted, the slots in the sizer head allow for visualization of the coronoid CO (FIG. 6A) to confirm that the ulnohumeral joint is reduced when measurements are made. If a gap (e.g., G, FIG. 6B) is visualized, this suggests that the length of the proposed implant is too long or over-stuffed.

A further step includes using trials of the actual head sizes and stem lengths to perform final evaluation of the size and length, using one or more spacers (not shown) to achieve a desired extension as necessary. The radial head system provides spacers to set this distance prior to locking the shaft in the stem portion with a set screw. For the 1 mm length position, only the first spacer of 1 mm is used. For the 3 mm length position, the first spacer and a 2 mm second spacer are used together.

Subsequent steps may include optionally performing intraoperative radiographs to confirm appropriate size and position of the implant, inserting the stem of the permanent implant of the same size as the appropriate trial implant, and attaching the radial head. Once in the correct position by use of the spacers, a set screw may be placed in the implant (e.g., 10, FIG. 2A) to lock the radial head (e.g., 12, FIG. 2A) and stem portion (e.g., 14, FIG. 2A) in the selected relative positions. The surrounding tissues may be repaired and the surgical wound site may be closed. An optional radiograph for final evaluation may be obtained. More details of the surgical procedures are described in U.S. Pat. No. 7,740,661, the disclosure of which is incorporated herein by reference in its entirety.

Figure 10:
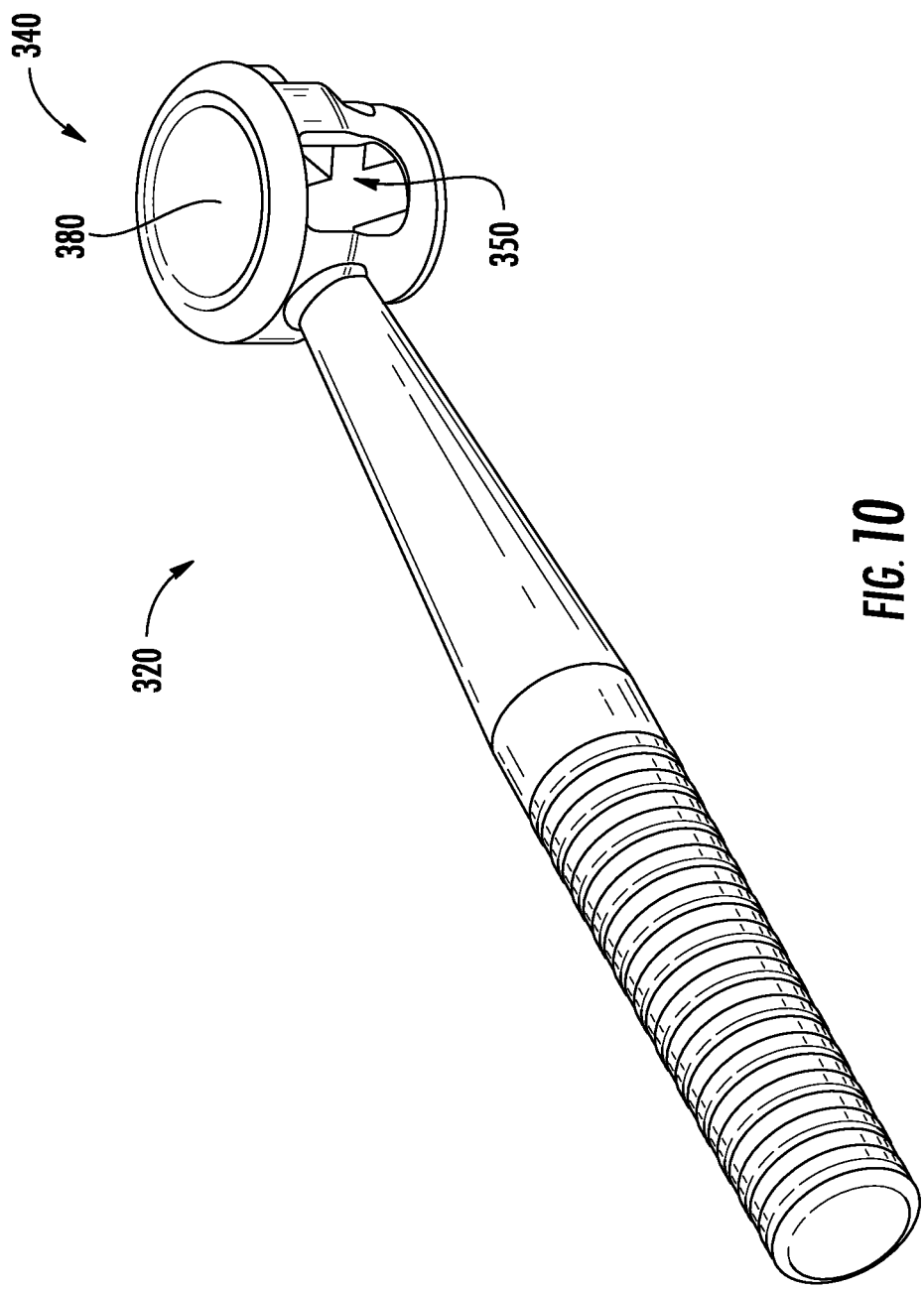
FIG. 10 is a perspective view of an orthopedic implant sizing instrument according to a further exemplary embodiment of the subject matter described herein.
Figure 11:
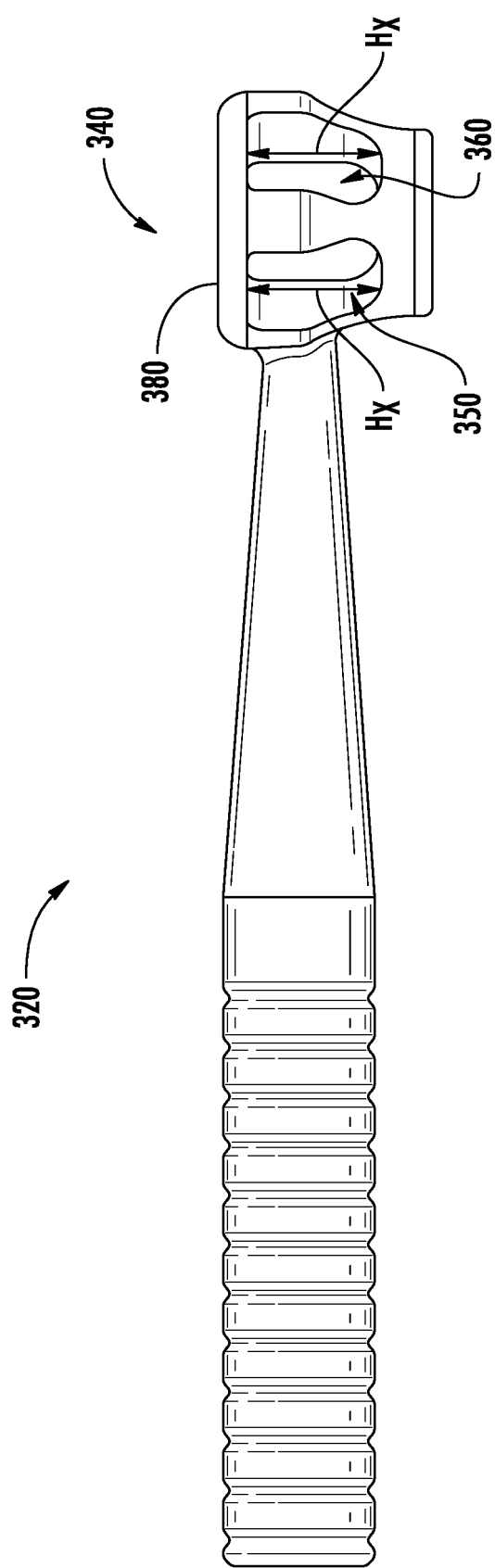
FIG. 11 a front elevational view of the orthopedic implant sizing instrument shown in FIG. 10.

FIGS. 10 and 11 are alternative embodiments of a sizing instrument generally designated 320. Sizing instrument 320 comprises a single sizer head 340 having a plurality of windows 350, 360 disposed therein. Notably, the windows 350, 360 do not intersect the upper surface of the sizer head. As FIG. 11 illustrates, each window 350, 360 has a height $H_X$ from a point below an upper surface of the sizer head to a point above a lower surface of the sizer head without intersecting the upper surface or lower surface such that the upper surface forms a closed upper cover 380 of the sizer head 340. Sizer head 340 comprises a hollow center, with one or more openings in the peripheral wall providing for visibility therethrough.

Figure 12:
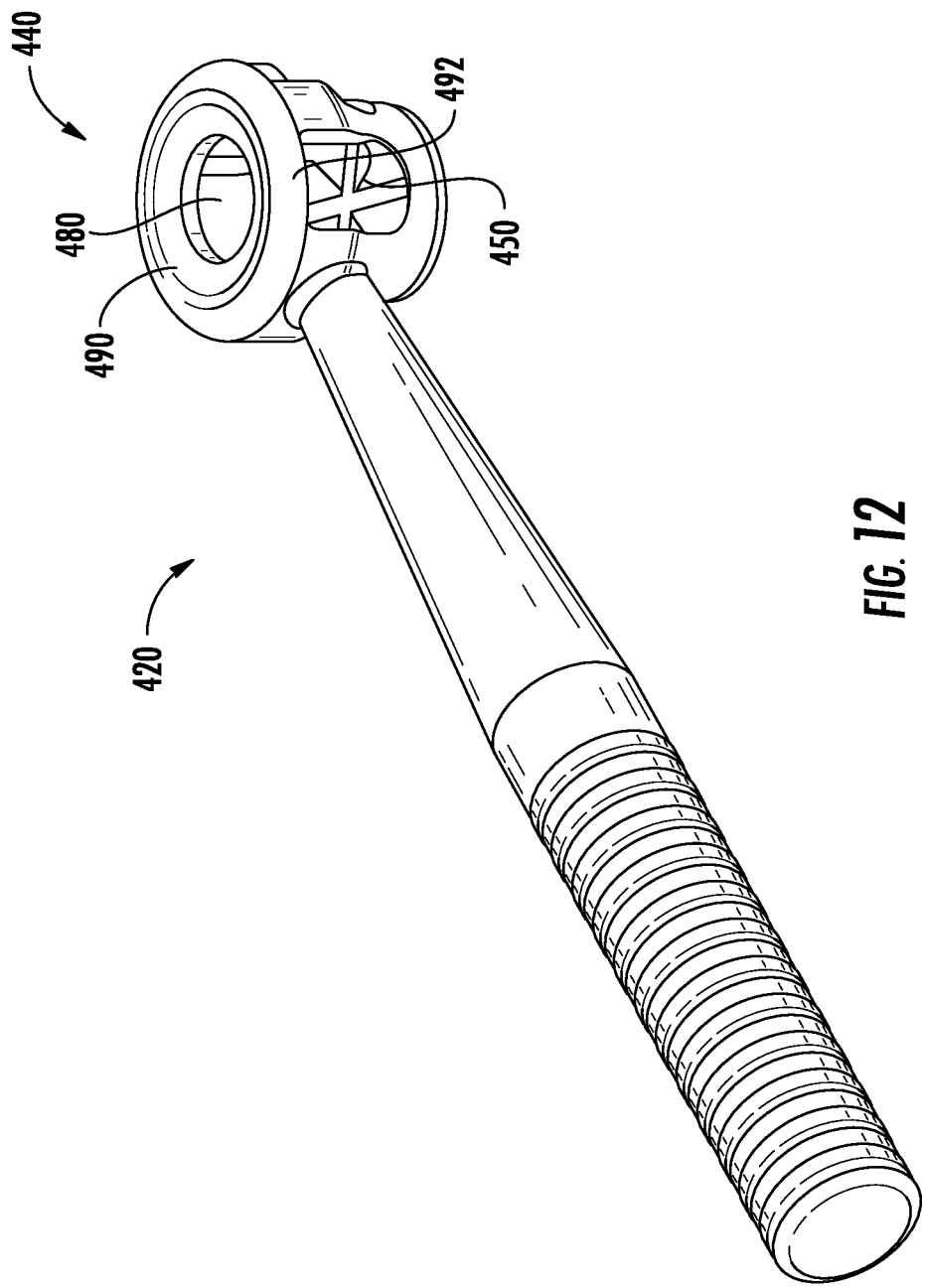
FIG. 12 is a perspective view of an orthopedic implant sizing instrument according to a further exemplary embodiment of the subject matter described herein.
Figure 13:
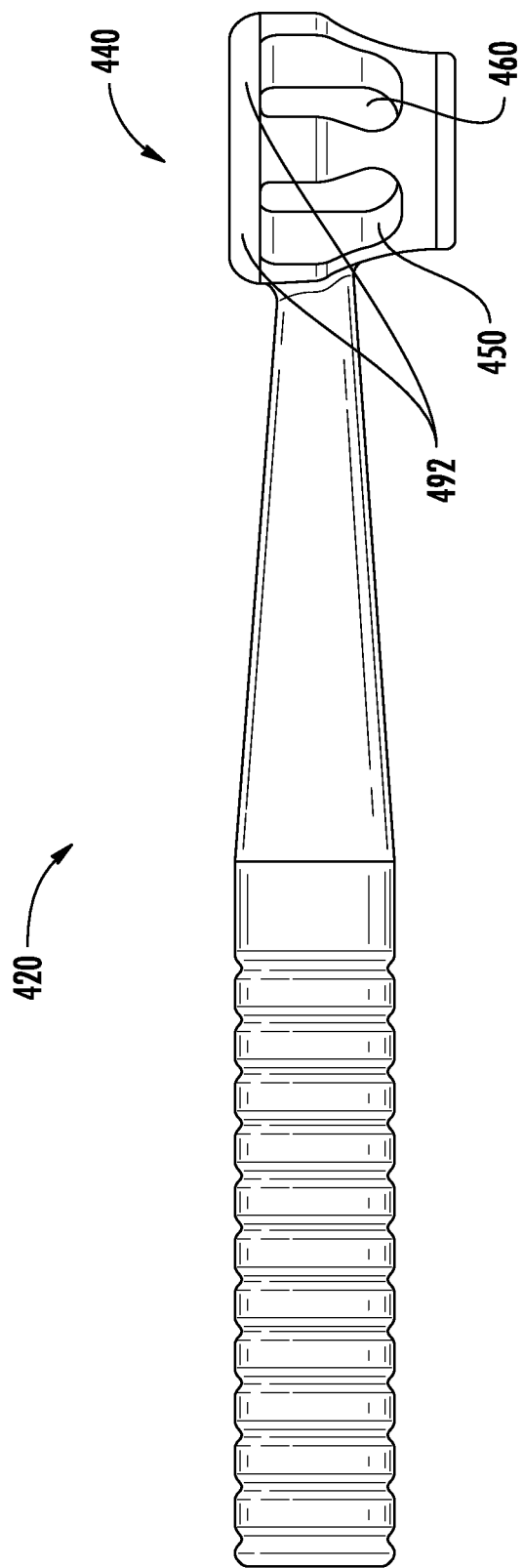
FIG. 13 a front elevational view of the orthopedic implant sizing instrument shown in FIG. 12.

FIGS. 12 and 13 are alternative embodiments of a sizing instrument generally designated 420. Sizing instrument 420 comprises a single sizer 440 head having a plurality of windows 450, 460 disposed therein. Windows 450, 460 at least partially intersect an upper surface of the sizer head 440. The upper surface has an aperture 480 disposed therein that intersects windows 450, 460, such that the upper surface of the sizer head forms a partial cover 490 of the sizer head and upper edges 492 of the windows. The aperture 480 may include a centrally disposed aperture and may be in any circular or non-circular shape.

Figure 14:
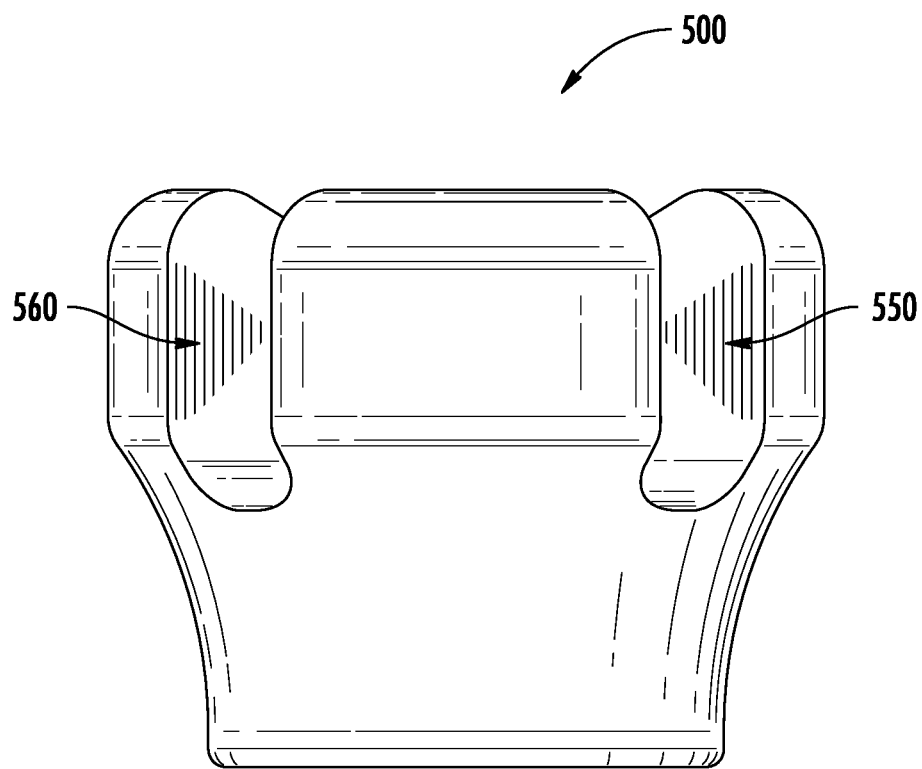
FIG. 14 is a front view of a standalone sizer head according to a further exemplary embodiment of the subject matter described herein.

FIG. 14 is a front view of a standalone sizer head generally designated 500 according to a further exemplary embodiment of the subject matter described herein. Sizer head 500 is devoid of an elongated member or handle. As shown in FIG. 14, like the sizer heads (e.g., 40, 70, etc.) described above with respect to the orthopedic implant sizing instrument, sizer head 500 is a trial implant having multiple windows 550, 560 disposed therein that allows visualization or sight therethrough. In the embodiment shown, the multiple windows 550, 560 intersect at an approximately 90° angle. It is contemplated that two windows 550, 560 in a standalone sizer head may intersect with each other at more than 0° up to 90°, preferably from 30° to 90°. All the descriptions and variations of the sizer heads discussed above with respect to the sizing instruments apply to the standalone sizer head 500 as well, where applicable, unless stated otherwise. Sizer head 500 may be configured and used as a trial implant. The one or more transverse windows 550, 560 in the sizer head allows a user to view through the trial to look at a bone behind it, which is usually a different bone from the underlying bone that the sizer head or trial implant fits on.

The sizing instruments (e.g., 20, 120, 220, 420, and 500) of the present subject matter may be made of any biocompatible material, for example, any metal or synthetic polymer materials. Exemplary materials include, but are not limited to, stainless steel, anodized aluminum, titanium, polyether ether ketone (PEEK), polyetherimide resins, polyphenylsulfone, and acetal resin. The sizing instruments can be manufactured via machining from bar stock or any other conventional manufacturing methods.

The orthopedic implant sizing instruments, systems, and methods described herein may be used in arthroplasty procedures to assess whether an elbow joint (FIG. 1) is properly reduced prior to surgical implantation of an implant (10, FIG. 2A, 2B). Orthopedic implant sizing instruments, systems, and methods described herein may be useful in assessing any other joint and/or bone surfaces thereof where it is difficult to assess whether the joint is properly reduced. For example, the sizing instrument may be used with the Katalyst™ radial head system, any other radial head arthroplasty systems, ulnar head replacements in the wrist, and/or in any joint where two or more bones are involved.

The orthopedic implant sizing instruments and systems herein may be used to provide a method for sizing an orthopedic implant (e.g., 10, FIG. 2A). The method comprises providing a sizer head having an upper surface and a lower surface surrounded by a peripheral wall that extends between the upper surface and the lower surface. The method further comprises providing or using a first window that extends from a first point on the peripheral wall to a second point on the peripheral wall to provide visibility therethrough. The method further comprises placing the sizer head proximate to one or more surgically exposed bones of an elbow joint and looking through the first window to determine an appropriate implant size.

Other embodiments of the current subject matter will be apparent to those skilled in the art from a consideration of this specification or practice of the subject matter disclosed herein. Thus, the foregoing specification is considered merely exemplary of the current subject matter with the true scope thereof being defined by the following claims.

What is claimed is:

1. An orthopedic implant sizing instrument comprising: an elongated member having a longitudinal axis, a first end, and a second end; and a first sizer head disposed at the first end of the elongated member, wherein the first sizer head has an upper surface, a lower surface, and a peripheral wall that extends between the upper surface and the lower surface, and wherein the first sizer head has a first head height, which is measured between the lower surface and the upper surface in a direction transverse to the longitudinal axis of the elongated member; wherein the first sizer head comprises a first window comprising a recessed channel disposed in the upper surface, extending from a first point on the peripheral wall to a second point on the peripheral wall for providing visibility therethrough; and wherein the elongated member is connected to the peripheral wall of the first sizer head.

2. The orthopedic implant sizing instrument of claim 1, wherein the first point on the peripheral wall diametrically opposes the second point on the peripheral wall.

3. The orthopedic implant sizing instrument of claim 1, wherein the first window bisects the upper surface of the first sizer head.

4. The orthopedic implant sizing instrument of claim 1, wherein the first sizer head comprises a second window which extends from a third point on the peripheral wall to a fourth point on the peripheral wall providing visibility therethrough.

5. The orthopedic implant sizing instrument of claim 4, wherein the third point on the peripheral wall diametrically opposes the fourth point on the peripheral wall.

6. The orthopedic implant sizing instrument of claim 4, wherein the first and second windows intersect each other at a 90° angle.

7. The orthopedic implant sizing instrument of claim 1, comprising a second sizer head connected to the second end of the elongated member, the second sizer head having an upper surface, a lower surface, a peripheral wall extending therebetween, a second head height, which is measured between the lower surface of the second sizer head and the upper surface of the second sizer head, and a first window, which extends from a first point on the peripheral wall of the second sizer head to a second point on the peripheral wall of the second sizer head for providing visibility therethrough.

8. The orthopedic implant sizing instrument of claim 7, wherein the second sizer head comprises a second window, which extends from a third point on the peripheral wall of the second sizer head to a fourth point on the peripheral wall of the second sizer head and is configured to provide visibility therethrough.

9. The orthopedic implant sizing instrument of claim 7, wherein the first sizer head differs from the second sizer head in an overall head height, an overall head diameter, a window depth, or any other geometrical aspect thereof.

10. The orthopedic implant sizing instrument of claim 7, wherein at least one of the first and second sizer heads are attachable and detachable to the elongated member.

11. The orthopedic implant sizing instrument of claim 7, wherein the first and second sizer heads are integrally formed with the elongated member.

12. The orthopedic implant sizing instrument of claim 1, wherein the upper surface and/or the lower surface of the first sizer head is oriented substantially parallel to the longitudinal axis of the elongated member.

13. The orthopedic implant sizing instrument of claim 1, wherein the first sizer head comprises a metal or synthetic polymer material.

14. An orthopedic implant sizing instrument set comprising a plurality of orthopedic implant sizing instruments according to claim 1.

15. An orthopedic implant sizing instrument comprising an elongated member having a longitudinal axis, a first end, and a second end; and a first sizer head connected to the first end of the elongated member, wherein the first sizer head has an upper surface, a lower surface, and a peripheral wall that extends between the upper surface and the lower surface, and wherein the first sizer head has a first head height, which is measured between the lower surface and the upper surface in a direction transverse to the longitudinal axis of the elongated member; wherein the first sizer head comprises: a first window comprising a recessed channel disposed in the upper surface, extending from a first point on the peripheral wall to a second point on the peripheral wall that diametrically opposes the first point, the first window having substantially parallel window walls; and a second window extending from a third point on the peripheral wall to a fourth point on the peripheral wall that diametrically opposes the third point, the second window having substantially parallel window walls; wherein the first window and the second window are perpendicular to each other.

16. The orthopedic implant sizing instrument of claim 15, wherein the upper surface and/or the lower surface of the first sizer head is oriented substantially parallel to the longitudinal axis of the elongated member.

17. The orthopedic implant sizing instrument of claim 15, wherein the first window bisects the upper surface of the first sizer head.

18. The orthopedic implant sizing instrument of claim 15, comprising a second sizer head connected to the second end of the elongated member, the second sizer head having an upper surface, a lower surface, a peripheral wall extending therebetween, a second head height, which is measured between the lower surface of the second sizer head and the upper surface of the second sizer head, and a first window, which extends from a first point on the peripheral wall of the second sizer head to a second point on the peripheral wall of the second sizer head for providing visibility therethrough.

19. The orthopedic implant sizing instrument of claim 18, wherein the second sizer head comprises a second window, which extends from a third point on the peripheral wall of the second sizer head to a fourth point on the peripheral wall of the second sizer head and is configured to provide visibility therethrough.

20. The orthopedic implant sizing instrument of claim 18, wherein the first sizer head differs from the second sizer head in an overall head height, an overall head diameter, a window depth, or any other geometrical aspect thereof.

21. The orthopedic implant sizing instrument of claim 18, wherein at least one of the first and second sizer heads are attachable and detachable the elongated member.

22. The orthopedic implant sizing instrument of claim 18, wherein the first and second sizer heads are integrally formed with the elongated member.

23. The orthopedic implant sizing instrument of claim 15, wherein the first sizer head comprises a metal or synthetic polymer material.

24. An orthopedic implant sizing instrument set comprising a plurality of orthopedic implant sizing instruments according to claim 15.

25. An orthopedic implant sizing instrument comprising: an elongated member having a longitudinal axis, a first end, and a second end; and a first sizer head disposed at the first end of the elongated member, wherein the first sizer head has an upper surface, a lower surface, and a peripheral wall that extends between the upper surface and the lower surface, wherein the upper surface and/or the lower surface of the first sizer head is oriented substantially parallel to the longitudinal axis of the elongated member, and wherein the first sizer head has a first head height, which is measured between the lower surface and the upper surface; wherein the first sizer head comprises a first window comprising a recessed channel disposed in the upper surface, extending from a first point on the peripheral wall to a second point on the peripheral wall for providing visibility therethrough; and wherein the elongated member is connected to the peripheral wall of the first sizer head.

26. The orthopedic implant sizing instrument of claim 25, wherein the first sizer head comprises a second window extending from a third point on the peripheral wall to a fourth point on the peripheral wall that diametrically opposes the third point, the second window having substantially parallel window walls, and wherein the first window and the second window are perpendicular to each other.

27. The orthopedic implant sizing instrument of claim 25, wherein the first point on the peripheral wall diametrically opposes the second point on the peripheral wall.

28. The orthopedic implant sizing instrument of claim 25, comprising a second sizer head connected to the second end of the elongated member, the second sizer head having an upper surface, a lower surface, a peripheral wall extending therebetween, a second head height, which is measured between the lower surface of the second sizer head and the upper surface of the second sizer head, and a first window, which extends from a first point on the peripheral wall of the second sizer head to a second point on the peripheral wall of the second sizer head for providing visibility therethrough.

29. The orthopedic implant sizing instrument of claim 28, wherein the second sizer head comprises a second window, which extends from a third point on the peripheral wall of the second sizer head to a fourth point on the peripheral wall of the second sizer head and is configured to provide visibility therethrough.

30. The orthopedic implant sizing instrument of claim 28, wherein the first sizer head differs from the second sizer head in an overall head height, an overall head diameter, a window depth, or any other geometrical aspect thereof.

31. The orthopedic implant sizing instrument of claim 28, wherein at least one of the first and second sizer heads are attachable and detachable to the elongated member or wherein the first and second sizer heads are integrally formed with the elongated member.

32. The orthopedic implant sizing instrument of claim 25, wherein the first window bisects the upper surface of the first sizer head.

33. The orthopedic implant sizing instrument of claim 25, wherein the first sizer head comprises a metal or synthetic polymer material.

34. An orthopedic implant sizing instrument set comprising a plurality of orthopedic implant sizing instruments according to claim 25.

35. A method for sizing an orthopedic implant using an orthopedic implant sizing instrument, the method comprising: placing an orthopedic implant sizing instrument proximate a surgical site; and determining an appropriate size of an orthopedic implant for use in the surgical site; wherein the orthopedic implant sizing instrument comprises a first sizer head having an upper surface, a lower surface, and a peripheral wall that extends between the upper surface and the lower surface; wherein the first sizer head comprises a first window comprising a recessed channel disposed in the upper surface, extending from a first point on the peripheral wall to a second point on the peripheral wall and providing visibility through the instrument from the first point to the second point on the peripheral wall when the first sizer head is placed proximate the surgical site; and wherein an elongated member is connected to the first sizer head at the peripheral wall thereof.

36. The method of claim 35, wherein the first point on the peripheral wall diametrically opposes the second point on the peripheral wall.

37. The method of claim 35, wherein the first window bisects the upper surface of the first sizer head.

38. The method of claim 35, wherein the first sizer head comprises a second window which extends from a third point on the peripheral wall to a fourth point on the peripheral wall providing visibility therethrough.

39. The method of claim 38, wherein the third point on the peripheral wall diametrically opposes the fourth point on the peripheral wall.

40. The method of claim 38, wherein the first and second windows intersect each other at a 90° angle.

41. The method of claim 35, wherein the orthopedic implant sizing instrument comprises a second sizer head connected to the second end of the elongated member, the second sizer head having an upper surface, a lower surface, a peripheral wall extending therebetween, a second head height, which is measured between the lower surface of the second sizer head and the upper surface of the second sizer head, and a first window, which extends from a first point on the peripheral wall of the second sizer head to a second point on the peripheral wall of the second sizer head for providing visibility therethrough.

42. The method of claim 41, wherein the second sizer head comprises a second window, which extends from a third point on the peripheral wall of the second sizer head to a fourth point on the peripheral wall of the second sizer head and is configured to provide visibility therethrough.

43. The method of claim 41, wherein the first sizer head differs from the second sizer head in an overall head height, an overall head diameter, a window depth, or any other geometrical aspect thereof.

44. The method of claim 41, wherein at least one of the first and second sizer heads are attachable and detachable with the elongated member.

45. The method of claim 41, wherein the first and second sizer heads are integrally formed with the elongated member.

46. The method of claim 35, wherein the first sizer head comprises a metal or synthetic polymer material.

47. The method of claim 35, wherein the upper surface and/or the lower surface of the first sizer head is oriented substantially parallel to a longitudinal axis of the elongated member.

* * * * *